(12) United States Patent
Kim

(10) Patent No.: US 9,848,865 B2
(45) Date of Patent: Dec. 26, 2017

(54) SUTURE THREAD

(71) Applicant: Y.JACOBS MEDICAL INC., Seoul (KR)

(72) Inventor: Young Jae Kim, Seoul (KR)

(73) Assignee: Y.Jacobs Medical Inc., Seoul (KR)

(*) Notice: Subject to any disclaimer, the term of this patent is extended or adjusted under 35 U.S.C. 154(b) by 0 days.

(21) Appl. No.: 14/840,520

(22) Filed: Aug. 31, 2015

(65) Prior Publication Data

US 2015/0366553 A1 Dec. 24, 2015

Related U.S. Application Data

(62) Division of application No. 14/003,390, filed as application No. PCT/KR2012/001643 on Mar. 7, 2012.

(30) Foreign Application Priority Data

Mar. 7, 2011 (KR) .................. 10-2011-0019895
Jun. 29, 2011 (KR) .................. 10-2011-0064084

(51) Int. Cl.
*A61B 17/04* (2006.01)
*A61B 17/06* (2006.01)
*A61B 17/062* (2006.01)

(52) U.S. Cl.
CPC ............ *A61B 17/04* (2013.01); *A61B 17/062* (2013.01); *A61B 17/06004* (2013.01); *A61B 17/06109* (2013.01); *A61B 17/06166* (2013.01); *A61B 17/0401* (2013.01); *A61B 2017/0448* (2013.01); *A61B 2017/0464* (2013.01); *A61B 2017/06028* (2013.01); *A61B 2017/06176* (2013.01)

(58) Field of Classification Search
CPC .............. A61B 17/04; A61B 17/0401; A61B 17/06004; A61B 17/06109; A61B 17/06166

See application file for complete search history.

(56) References Cited

U.S. PATENT DOCUMENTS

| 3,123,077 A | 3/1964 | Alcamo |
| 3,981,307 A | 9/1976 | Borysko |
| 4,744,364 A | 5/1988 | Kensey |

(Continued)

FOREIGN PATENT DOCUMENTS

| CN | 101219066 A | 7/2008 |
| CN | 2012166619 Y | 4/2009 |

(Continued)

OTHER PUBLICATIONS

BD Product Catalog, Jan. 2010, BD Medical.

(Continued)

*Primary Examiner* — Julie A Szpira
(74) *Attorney, Agent, or Firm* — Knobbe Martens Olson & Bear LLP

(57) ABSTRACT

A suture thread is used to perform suturing without tying part of or the whole of knots that are supposed to be tied during suturing. A suture thread support body prevents an end of the suture thread from being pulled into a suturing site. A needle accommodation body has a shape of a tube having a through-hole through both ends. The suture thread has the suture thread support body and the needle accommodation body.

7 Claims, 7 Drawing Sheets

(56) References Cited

U.S. PATENT DOCUMENTS

| | | | |
|---|---|---|---|
| 4,805,292 A * | 2/1989 | Noguchi | A61B 17/06004 163/5 |
| 4,922,904 A * | 5/1990 | Uetake | A61B 17/06004 163/1 |
| 4,932,962 A * | 6/1990 | Yoon | A61B 17/0469 606/224 |
| 5,041,129 A | 8/1991 | Hayhurst et al. | |
| 5,053,046 A | 10/1991 | Janese | |
| 5,053,047 A | 10/1991 | Yoon | |
| 5,080,667 A * | 1/1992 | Chen | A61B 17/06004 606/225 |
| 5,192,301 A | 3/1993 | Kamiya et al. | |
| 5,207,694 A | 5/1993 | Broome | |
| 5,224,955 A * | 7/1993 | West | A61B 17/06004 163/1 |
| 5,236,443 A * | 8/1993 | Sontag | A61B 17/0482 606/223 |
| 5,259,846 A * | 11/1993 | Granger | A61B 17/06 606/223 |
| 5,269,809 A | 12/1993 | Hayhurst et al. | |
| 5,330,503 A | 7/1994 | Yoon | |
| 5,500,000 A | 3/1996 | Feagin | |
| 5,626,614 A | 5/1997 | Hart | |
| 5,643,295 A * | 7/1997 | Yoon | A61B 17/0483 606/151 |
| 5,683,417 A | 11/1997 | Cooper | |
| 5,741,299 A | 4/1998 | Rudt | |
| 5,931,855 A | 8/1999 | Buncke et al. | |
| 6,241,747 B1 | 6/2001 | Ruff | |
| 6,939,326 B1 | 9/2005 | Thappa | |
| 7,056,331 B2 | 6/2006 | Kaplan et al. | |
| 7,468,068 B2 | 12/2008 | Kolster | |
| 7,582,105 B2 | 9/2009 | Kolster | |
| 7,601,164 B2 | 10/2009 | Wu | |
| 7,967,841 B2 | 6/2011 | Yuan et al. | |
| 7,988,727 B2 | 8/2011 | Santamore et al. | |
| 8,192,462 B2 | 6/2012 | Sulamanidze et al. | |
| 8,747,438 B2 | 6/2014 | Longo et al. | |
| 8,758,367 B2 | 6/2014 | Philippon et al. | |
| 9,044,224 B2 | 6/2015 | Lauria | |
| 9,125,647 B2 | 9/2015 | Goraltchouk et al. | |
| 9,204,965 B2 | 12/2015 | Longoria | |
| 9,675,341 B2 | 6/2017 | D'Agostino et al. | |
| 2002/0198544 A1 | 12/2002 | Uflacker | |
| 2003/0149447 A1* | 8/2003 | Morency | A61B 17/06166 606/228 |
| 2004/0030319 A1 | 2/2004 | Korkor et al. | |
| 2004/0153102 A1* | 8/2004 | Therin | A61B 17/0401 606/144 |
| 2005/0101984 A1 | 5/2005 | Chanduszko et al. | |
| 2005/0240224 A1 | 10/2005 | Wu | |
| 2005/0245963 A1 | 11/2005 | Kida et al. | |
| 2006/0079935 A1 | 4/2006 | Kolster | |
| 2006/0135994 A1 | 6/2006 | Ruff et al. | |
| 2006/0135996 A1 | 6/2006 | Schwartz et al. | |
| 2006/0265010 A1 | 11/2006 | Paraschac et al. | |
| 2007/0038249 A1 | 2/2007 | Kolster | |
| 2007/0167958 A1 | 7/2007 | Sulamanidze et al. | |
| 2007/0213770 A1 | 9/2007 | Dreyfuss | |
| 2008/0058816 A1 | 3/2008 | Philippon et al. | |
| 2008/0132943 A1 | 6/2008 | Maiorino et al. | |
| 2008/0228144 A1 | 9/2008 | Liniger et al. | |
| 2008/0281357 A1 | 11/2008 | Sung et al. | |
| 2009/0088797 A1 | 4/2009 | Crombie et al. | |
| 2009/0093670 A1 | 4/2009 | Annest et al. | |
| 2009/0112259 A1 | 4/2009 | D'Agostino | |
| 2009/0210003 A1 | 8/2009 | Sulamanidze et al. | |
| 2009/0299407 A1 | 12/2009 | Yuan et al. | |
| 2010/0137679 A1 | 6/2010 | Lashinski et al. | |
| 2010/0160961 A1 | 6/2010 | Nawrocki et al. | |
| 2011/0054522 A1 | 3/2011 | Lindh et al. | |
| 2011/0238111 A1 | 9/2011 | Frank | |
| 2011/0270304 A1 | 11/2011 | Lee | |
| 2011/0282386 A1 | 11/2011 | Friedrich et al. | |
| 2011/0288563 A1 | 11/2011 | Gianotti et al. | |
| 2012/0109193 A1 | 5/2012 | Primavera et al. | |
| 2012/0109195 A1 | 5/2012 | Odermatt et al. | |
| 2012/0239002 A1 | 9/2012 | Griswold | |
| 2013/0245684 A1 | 9/2013 | Ruff et al. | |
| 2013/0345745 A1 | 12/2013 | Kim | |
| 2014/0155913 A1 | 6/2014 | Kim | |
| 2014/0228971 A1 | 8/2014 | Kim | |
| 2014/0364904 A1 | 12/2014 | Kim | |
| 2015/0305736 A1 | 10/2015 | Kim | |
| 2016/0302905 A1 | 10/2016 | Kim | |

FOREIGN PATENT DOCUMENTS

| | | |
|---|---|---|
| CN | 101500495 A | 8/2009 |
| CN | 102271734 A | 12/2011 |
| DE | 3223153 C1 | 8/1983 |
| DE | 102008057213 A1 | 5/2010 |
| EP | 0314412 A1 | 5/1989 |
| EP | 1929961 A2 | 6/2008 |
| EP | 1955720 A1 | 8/2008 |
| EP | 2020209 A1 | 2/2009 |
| EP | 2108316 A1 | 10/2009 |
| EP | 2386252 A1 | 11/2011 |
| EP | 2386323 A2 | 11/2011 |
| GB | 1091282 A | 11/1967 |
| JP | 04-307050 A | 10/1992 |
| JP | 04-307052 A | 10/1992 |
| JP | 08-52124 A | 2/1996 |
| JP | 08-140982 A | 6/1996 |
| JP | 02-277459 B2 | 5/1998 |
| JP | 10-258123 A | 9/1998 |
| JP | 10-272182 A | 10/1998 |
| JP | 2000-202029 A | 7/2000 |
| JP | 3069906 U | 7/2000 |
| JP | 2000-225118 A | 8/2000 |
| JP | 2000-232984 A | 8/2000 |
| JP | 2002-516585 A | 6/2002 |
| JP | 2003-019683 A | 1/2003 |
| JP | 2004-041492 A | 2/2004 |
| JP | 2004-057516 A | 2/2004 |
| JP | 2004-073403 A | 3/2004 |
| JP | 2004-121634 A | 4/2004 |
| JP | 2004-530524 A | 10/2004 |
| JP | 2004-329964 A | 11/2004 |
| JP | 2005-177499 A | 7/2005 |
| JP | 2005-177500 A | 7/2005 |
| JP | 2006-025867 A | 2/2006 |
| JP | 2006-515203 A | 5/2006 |
| JP | 2007-075616 A | 3/2007 |
| JP | 2007-090062 A | 4/2007 |
| JP | 2007-537017 A | 12/2007 |
| JP | 2008-114074 A | 5/2008 |
| JP | 2008-514382 A | 5/2008 |
| JP | 2008-132327 A | 6/2008 |
| JP | 2008-132328 A | 6/2008 |
| JP | 2008-132329 A | 6/2008 |
| JP | 2008-546454 A | 12/2008 |
| JP | 2009-517156 A | 4/2009 |
| JP | 2009-531071 A | 9/2009 |
| JP | 2009-247890 A | 10/2009 |
| JP | 2009-279393 A | 12/2009 |
| JP | 2010-500102 A | 1/2010 |
| JP | 2010-507453 A | 3/2010 |
| JP | 2010-518902 A | 6/2010 |
| JP | 2010-537676 A | 12/2010 |
| JP | 2011-500208 A | 1/2011 |
| JP | 2011-240133 A | 12/2011 |
| JP | 2011-240134 A | 12/2011 |
| JP | 2012-515015 A | 7/2012 |
| KR | 10-0178358 B1 | 4/1998 |
| KR | 20-0287634 Y1 | 8/2002 |
| KR | 20-0320005 Y1 | 7/2003 |
| KR | 10-0473108 B1 | 3/2005 |
| KR | 10-2005-0108494 A | 11/2005 |
| KR | 10-0761921 B1 | 10/2007 |
| KR | 10-2008-0039345 A | 5/2008 |
| KR | 10-2009-0035692 A | 4/2009 |
| KR | 10-2009-0103639 A | 10/2009 |

(56) References Cited

FOREIGN PATENT DOCUMENTS

| | | |
|---|---|---|
| KR | 10-2010-0120642 A | 11/2010 |
| KR | 20-0451570 Y1 | 12/2010 |
| KR | 10-2011-0019895 A | 3/2011 |
| KR | 10-1044731 B1 | 6/2011 |
| KR | 10-1057376 B1 | 8/2011 |
| KR | 10-1105647 B1 | 1/2012 |
| KR | 10-2012-0010049 A | 2/2012 |
| KR | 10-1132841 B1 | 4/2012 |
| KR | 10-1155817 B1 | 6/2012 |
| KR | 10-1182337 B1 | 9/2012 |
| KR | 10-1185583 B1 | 9/2012 |
| KR | 10-1326736 B1 | 11/2013 |
| KR | 10-1367902 B1 | 2/2014 |
| KR | 10-1455206 B1 | 10/2014 |
| SU | 700121 A1 | 11/1979 |
| SU | 1178420 A1 | 2/1984 |
| SU | 1360705 A1 | 7/1986 |
| WO | 2007/098212 A2 | 8/2007 |
| WO | 2008/020937 A2 | 2/2008 |
| WO | 2008/057261 A2 | 5/2008 |
| WO | 2008/103308 A1 | 8/2008 |
| WO | 2009/027883 A2 | 3/2009 |
| WO | 2009/055105 A1 | 4/2009 |
| WO | 2010/028324 A2 | 3/2010 |
| WO | 2010/052006 A1 | 5/2010 |
| WO | 2010/062743 A | 6/2010 |
| WO | 2010/080014 A | 7/2010 |
| WO | 2011/128392 A1 | 10/2011 |
| WO | 2012/144677 A1 | 10/2012 |
| WO | 2013/169075 A1 | 11/2013 |
| WO | 2015/083864 A1 | 6/2015 |

OTHER PUBLICATIONS

"Optinova ICM (TM) IV-catheter tubing", 2007, Optimus Nova.
John Jacobs Medical, "Youngs Lift", Jun. 7, 2012.
"Catheter", http://ko.wikipedia.org/wiki/%EC%B9%B4%ED%85%8C%ED%84%B0?oldid=13222103, printed Aug. 24, 2015.
"I.V.Catheter, Product Introduction", http://www.dukwooco.co.kr/english/product/pro_1.htm, Dukwoo Medical Co., Ltd., printed on Apr. 9, 2016.
Prado et al., "Supplemental Fixation After Endoscopic Brow Elevation Using a Single Nylon Suture", Printed from QMP's Plastic Surgery Pulse News, 2010, vol. 2, No. 1, Quality Medical Publishing, St. Louis, obtained from http://www.plasticsurgerypulsenews.com/2/article_dtl.php?QnCategoryID=18QnArticleID=45.
"Polydioxanone Suture", Metro Korea, downloaded from http://www.metrokr.com/shop/goods/goods_view.php?goodsno=186785506&category=004 on or before Oct. 30, 2015.
"Safelock Catheter", Lkmedical Co., Ltd. Product Catalog, downloaded from http://www.lkmedical.com on or before Oct. 30, 2015.
"Qosina, Thousands of Stock Components," 2014, Qosina Product Catalog.
"Angiocatheter", http://medical-dictionary.thefreedictionary.com/angiocatheter, The Free Dictionary, downloaded on or before Oct. 2, 2015.
"Food and drug safety-wife medical equipment e-petitions", Ministry of Food and Drug Safety, downloaded from https://www.emed.mfds.go.kr/, on or before Nov. 3, 2015.
Office Communication Japanese Patent Office on third party submission of references in Japanese Patent Application 2014-549981 dated Jan. 25, 2016—20 pages.
Product Photos, Jul. 18, 2006, BD Inc., downloaded on or before Oct. 8, 2014.
"MediFirst Homepage", http://www.medifirst.co.kr, printed on or before Nov. 5, 2013.
Karam et al., "Curved Stylet Core Biopsy Results in Larger Cores", American Journal of Roentgenology, Jul. 2010, vol. 195, pp. 242-244.
Application of related U.S. Appl. No. 15/102,240.
Japanese Office Action dated Jun. 30, 2016 of Japanese Patent Application No. 2014-207825 corresponding to related U.S. Appl. No. 14/003,390—2 pages.
uropean Office Action dated May 29, 2017 of corresponding European Patent Application No. 12755259.4—6 pages.
merriram-webster.com, stylet definition; retrieved May 4, 2015.

* cited by examiner

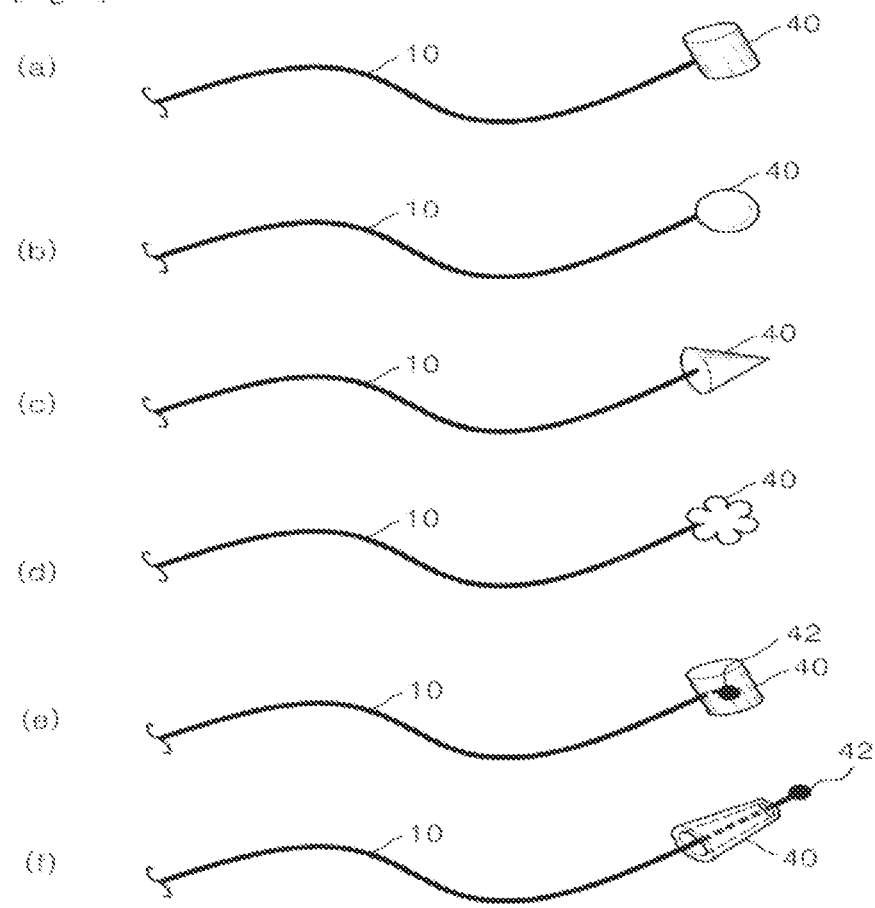
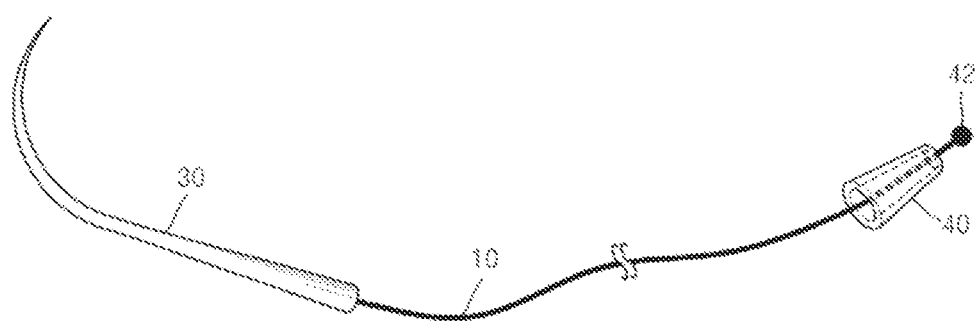

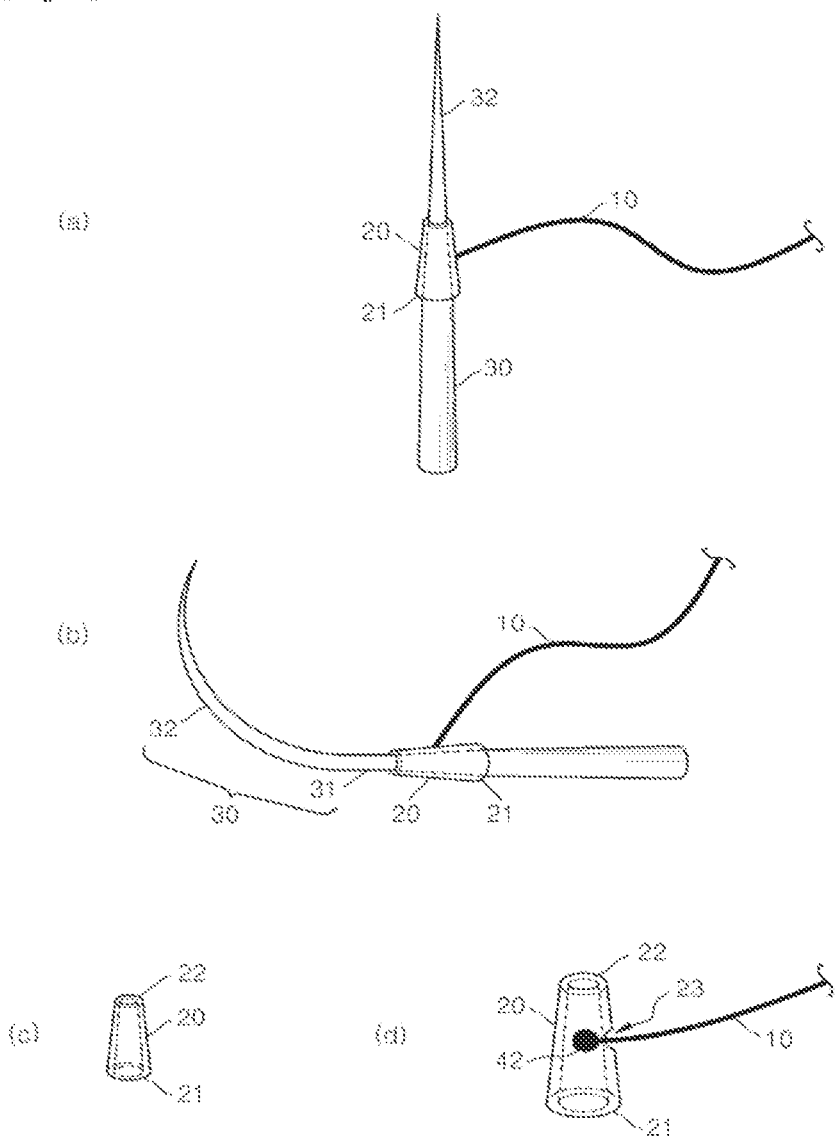

[Fig. 4]
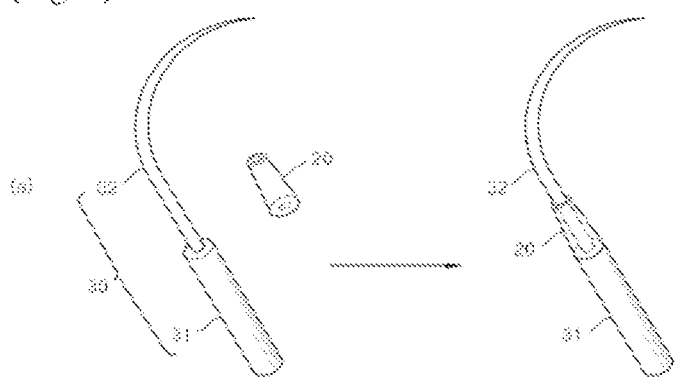
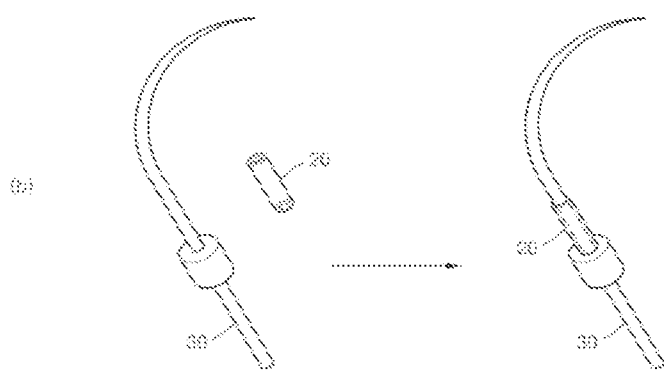
[Fig. 5]
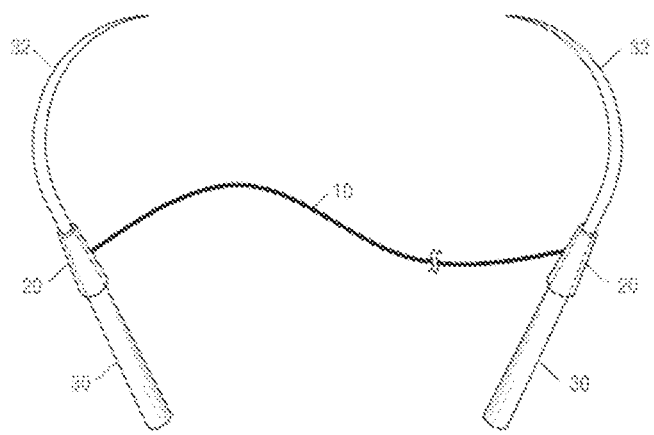

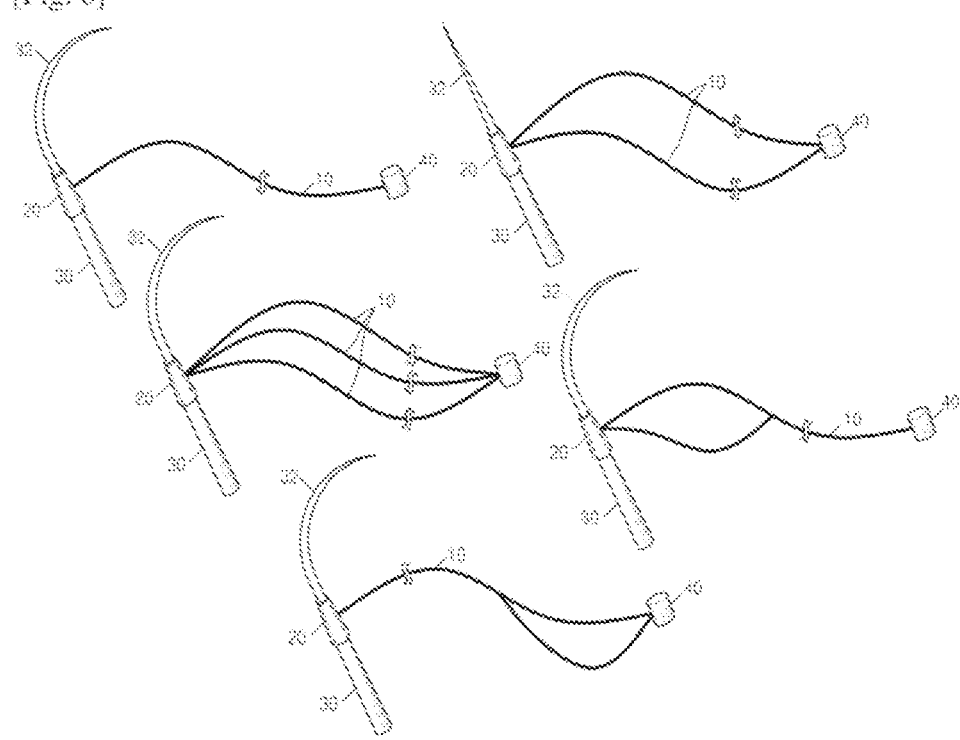

[Fig. 7]
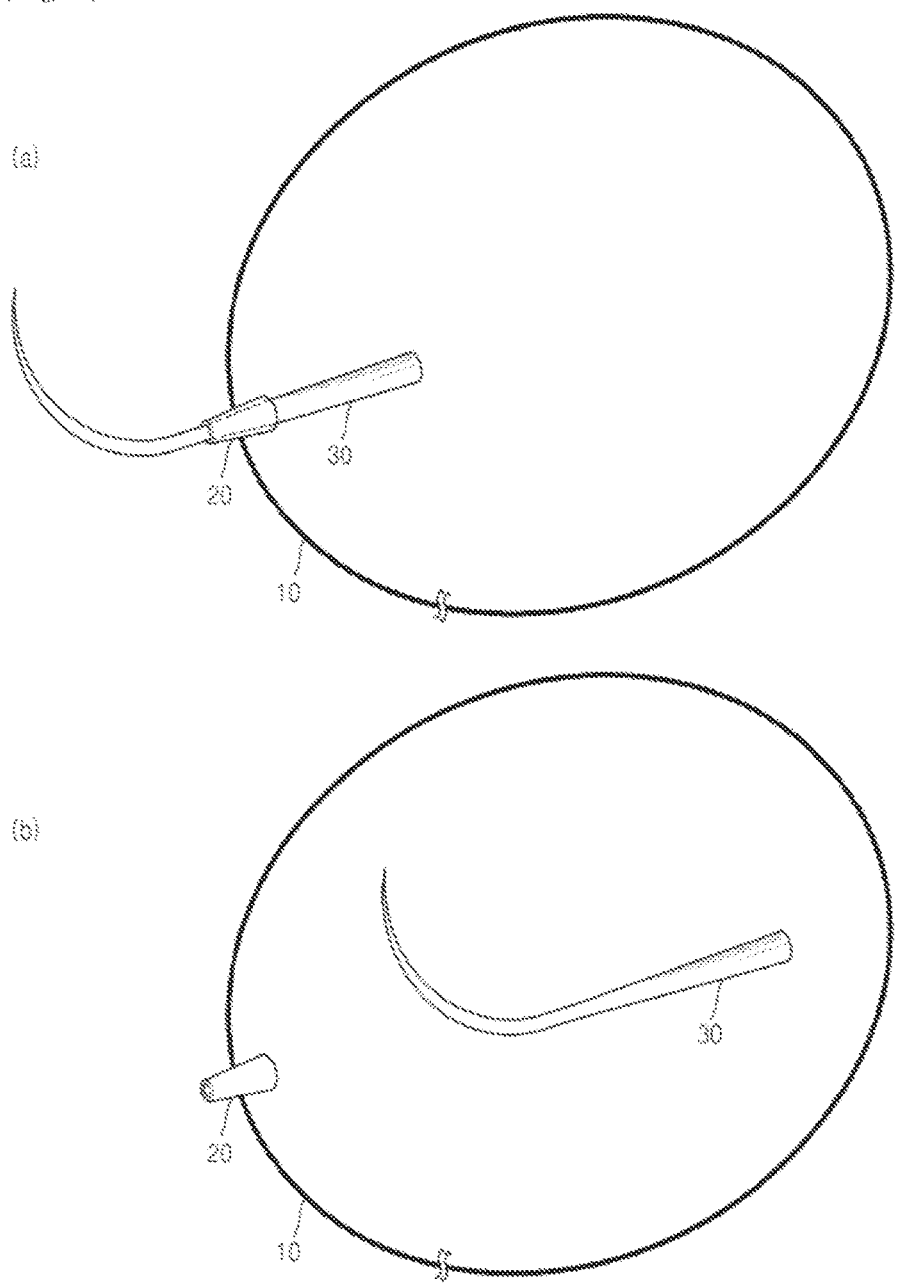

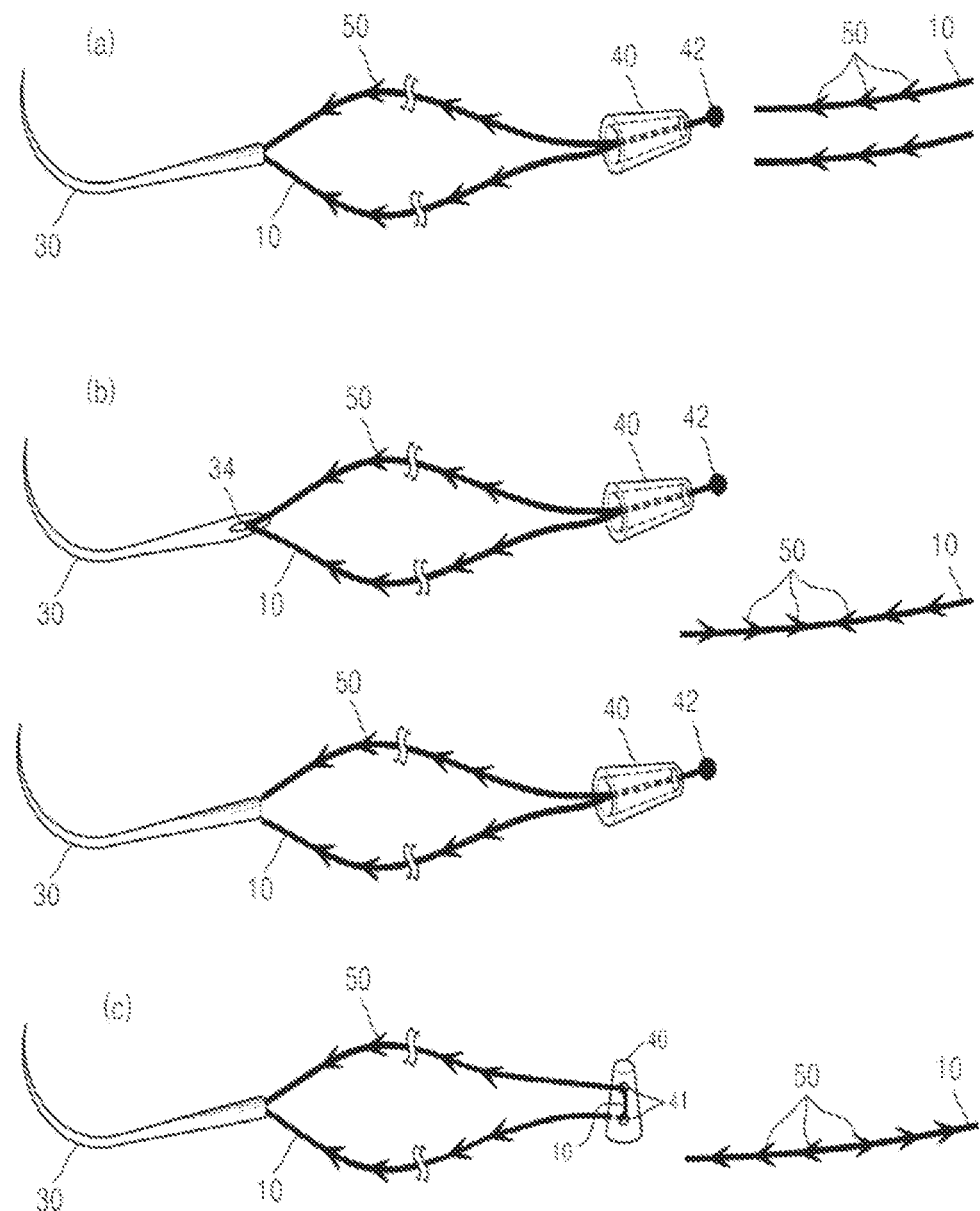

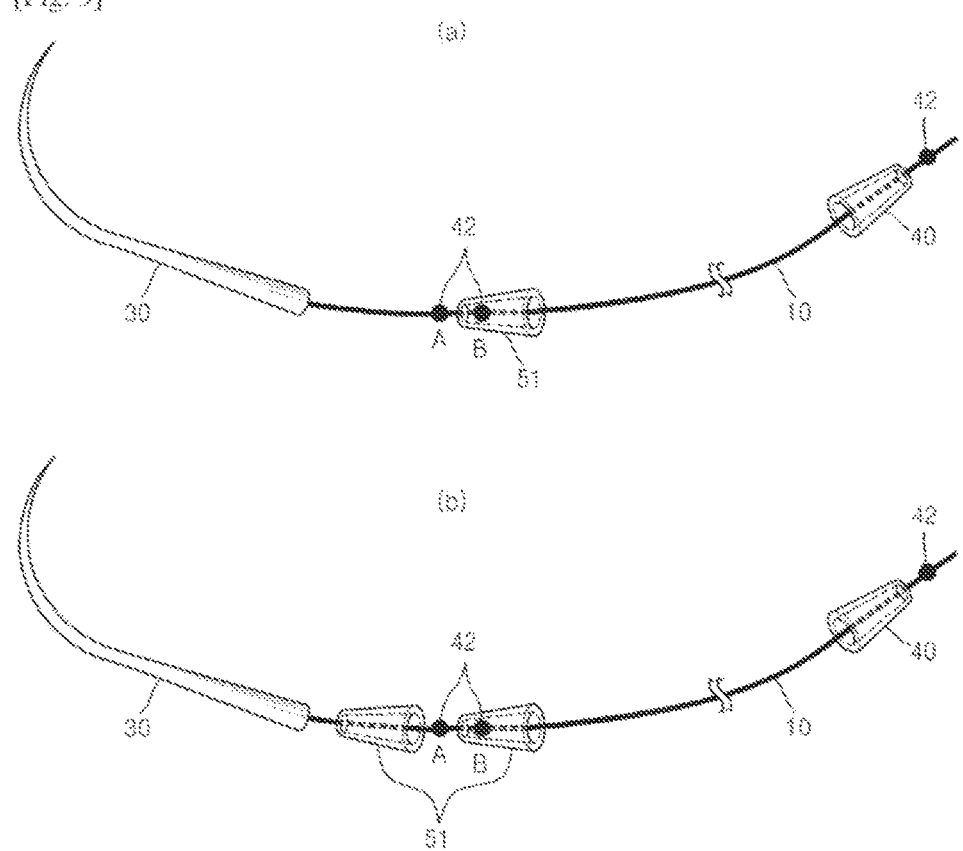

SUTURE THREAD

This application is a divisional application of U.S. application Ser. No. 14/003,390 filed on Sep. 5, 2013, which is a national phase application under 35 USC §371 of PCT International Patent Application No. PCT/KR2012/001643 filed on Mar. 7, 2012, which claims the benefit of priority from Korean Patent Application Nos. 10-2011-0019895 filed on Mar. 7, 2011 and 10-2011-0064084 filed on Jun. 29, 2011.

TECHNICAL FIELD

The present invention relates to a suture thread used for a surgical operation and a suturing method using the suture thread, and more particularly, to a suture thread that does not require a knotting procedure during a suture operation, a method of manufacturing the suture thread, and a suturing method using the suture thread.

BACKGROUND ART

In a suturing process performed for various surgical operation such as suturing of damaged muscles, blood vessels, nerves, injuries, or surgical cuts, double eyelid surgery, wrinkles plastic surgery, etc. a time-consuming, annoying, and very important work greatly affecting a result of surgery is a process of tying a knot to prevent the release of a suture thread after suturing a suturing site. During a suturing process, a knot is provided to prevent the release of a suture at a start portion and an ending portion of a suture or at a middle portion if necessary.

Since to shorten an operation time and complete an operation as quick as possible is very important, suturing and knotting techniques are essential for stable and efficient operations. However, it is not easy to quickly tie a knot at a distance by using tools to bond a suturing site in a body during an operation using a laparoscope, an endoscope, or an arthroscope, for example.

Conventionally, to tie a knot of a suture thread during suturing, an operator uses two tools to fix or wrap a suture thread while holding the suture thread. Since a large space is needed to manipulate the two tools, an operator needs to be highly experienced to shorten a surgery suture time as short as possible within a limited space such as the abdominal cavity. Thus, a method and a suturing tool, for example, a tool having a great degree of freedom such as a Cambridge endo, a Real hand, a Radius surgical system, etc., or robots to easily, quickly, and firmly tie a suture thread into a knot in a limited space have been developed.

Japanese Patent Laid-open Publication No. 2006-25867 discloses a suture thread for a surgery in which a suture thread is woven to be hollow inside in a lengthwise direction and a suturing tip is coupled to both end portions of the suture thread. Japanese Patent Laid-open Publication No. 2003-19683 discloses a surgical robot for ligation and suturing to prevent damage to tissue of a living body. However, a surgical robot such as a Davinci robot system that may facilitate suturing and knotting in an endoscope operation is very expensive and requires a large installation space, which discourages a wide use thereof. Thus, there is a demand to develop a suturing method that may be easily used at a lower cost and a suture thread and needle to enable the method.

DETAILED DESCRIPTION OF THE INVENTION

Technical Problem

The present invention provides a method of quickly and easily suturing in a limited space in a surgical operation, a tool for the method (suture thread support body, needle accommodation body, a suture thread including suture thread support body and/or needle accommodation body), and a method of manufacturing the tool.

The present invention provides a suture thread developed to perform suturing without tying some or all of knots that are supposed to be tied during suturing, and a manufacturing method thereof, a suture thread support body needed therefor, a needling accommodation body, and a suturing method using the same.

Technical Solution

According to an aspect of the present invention, there is provided a support body for preventing a tip end of a suture thread from being pulled into skin or tissue during suturing, and a suture thread in which the support body is coupled to an end of the suture thread. The other end of the suture thread in which the support body is coupled to the end passes through skin or tissue of a suturing site by a suture needle and thus suturing is performed. When suturing with the suture thread, the support body works as a knot and thus the end of the suture thread to which the support body is coupled is fixed at a portion where the suturing starts. Thus, since there is no worry of untying of the suture, no more knotting is needed in a suturing process. Also, the end of the suture thread may be fixed to the skin or tissue more firmly than a case of a suture thread only having a knot.

According to another aspect of the present invention, there is provided a needle accommodation body having a shape of a tube having a through-hole through both ends, and a suture thread having the needle accommodation body. The needle accommodation body may have a shape of a truncated circular cone or truncated pyramid in which a diameter of a through-hole increases from one end portion to the other end portion or a shape of a circular column or a prism in which a diameter of a through-hole is constant. The needle accommodation body may be formed of a firm material or a flexible material if necessary. The suture needle is inserted in the needle accommodation body. The suture needle coupled to the needle accommodation body has a shape of part of the needle main body fitting to the through-hole of the needle accommodation body. The suture needle may have a shape in which part of the needle main body has a diameter larger than that of a bottom end portion of the needle accommodation body. The suture needle may be pulled from the bottom end portion of the needle accommodation body to be removed from the needle accommodation body. The suture needle is connected to the needle accommodation body.

According to another aspect of the present invention, there is provided a suture thread having a needle accommodation body and a suture needle in which part of the needle main body of the suture needle coupled to the needle accommodation body is formed larger than the bottom end portion (end portion having a relatively larger diameter) of the needle accommodation body. The needle accommodation body may have a shape of a tube having a through-hole through both ends, a shape of a truncated circular cone or truncated pyramid in which a diameter of a through-hole increases from one end portion to the other end portion, a shape of a circular column or a prism in which a diameter of a through-hole is constant. The suture thread is connected to the needle accommodation body. The suture needle may be pulled from the bottom end portion of the needle accommodation body to be removed from the needle accommodation body.

According to another aspect of the present invention, there is provided a method of manufacturing a support body and/or a needle accommodation body.

When the suture thread having the needle accommodation body is in use, in the final step of suturing, the suture needle is penetrated into or inserted into other tissue around a suturing site from the needle accommodation body into the tissue. Then, the suture needle is pulled from the bottom end of the needle accommodation body and thus removed therefrom. Accordingly, the needle accommodation body removed of the suture needle remains in the tissue and the suture thread used for suturing is still coupled to the needle accommodation body. As a result, a suture is not untied even without making a knot at a final portion of the suturing.

Advantageous Effects

According to the present invention, a suture thread may facilitate a stable suture without tying a knot. When a suture thread with a support body and/or needle accommodation body is in use, an effect of a firm knot may be obtained without spending time to tie a knot. Accordingly, a suture time may be remarkably reduced through a simple suture technique. Also, without employing a suturing technique requiring experience, a suture operation may be stably and easily performed.

Furthermore, when the suture thread according to the present invention is in use, since a suture operation may be completed with only one tool. Thus, even when an area to be treated using an endoscope is small, suture may be performed quickly and accurately.

Furthermore, when a suture thread, a suturing method, a needle accommodation body, and a support body of the present invention are made of a material that may be absorbed by a living body, a process of removing the elements after an operation may be unnecessary.

DESCRIPTION OF THE DRAWINGS

FIG. 1 illustrates suture threads having various support bodies according to embodiments of the present invention.

FIG. 2 illustrates a suture thread having a support body and a needle according to an embodiment of the present invention.

FIG. 3 illustrates a needle accommodation body according to an embodiment of the present invention and a suture thread having the needle accommodation body, in which (*a*) and (*b*) of FIG. 3 illustrate that a needle is inserted in a needle accommodation body that is coupled to a suture thread, (*c*) of FIG. 3 illustrates a needle accommodation body according to an embodiment of the present invention, and (*d*) of FIG. 3 illustrates coupling of a needle accommodation body and a suture thread.

FIG. 4 illustrates the shapes of a needle accommodation body and a needle according to another embodiment of the present invention;

FIG. 5 illustrates a suture thread with a needle accommodation body provided at each of both end portions.

FIG. 6 illustrates a variety of suture threads to which a support body and a needle accommodation body are coupled respectively to one end portion and the other end portion of a suture thread.

FIG. 7 illustrates that a suture thread forming a loop is connected to a needle accommodation body according to an embodiment of the present invention.

FIG. 8 illustrates a barbed suture thread according to an embodiment of the present invention.

FIG. 9 illustrates a suture thread with a cone and a knot according to an embodiment of the present invention.

LIST OF MAJOR REFERENCE NUMERALS

10: suture thread  20: needle accommodation body
21: bottom end portion of needle accommodation body
22: front end portion of needle accommodation body
23: hole of needle accommodation body
30: suture needle  31: needle main body
32: needle tip
33: stepped portion of needle main body
34: needle hole
40: support body  41: hole of support body
42: knot
50: barb  51: cone

BEST MODE

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, a needle portion is exaggerated for easy understanding of the invention. It may be understood that the length of a thread connected to a needle or a needle accommodation body is quite long in actual use.

FIG. 1 illustrates suture threads 10 having various support bodies 40 according to embodiments of the present invention. The support body has a diameter larger than that of the suture thread and a shape such as a stick, a ball, a circular column, a circular cone, a pyramid, a truncated circular cone or truncated pyramid, a disc, a plate, a polyhedron, etc. The present invention is not limited thereto and the support body may have any shape and size that supports the suture thread so that an end portion of the suture thread is prevented from being pulled into a suturing site. The support body may be a uniform solid matter or may have at least one hole in both end portions of the support body. For example, the support body is a truncated circular cone and has a through-hole through both ends of the support body. The diameter of the hole or cavity is greater than that of a suture thread in use. The support body may be formed of a material such as nylon, polypropylene, for example, MESH, poly(vinyldene fluoride), polyester, stainless steel, titanium, etc, that is not absorbed by a living body, but the present invention is not limited thereto. Also, the support body may be formed of an absorbable material according to a purpose thereof. For example, polylactic acid, polydiaxonone, copolymer of lactic acid and glycolic acid, etc. may be used, but the present invention is not limited thereto. When a material that may be absorbable by a living body is used, the support body does not need to be removed after suturing a human body.

A method of coupling the suture thread and the support body includes a method of melting and bonding an end portion of a suture thread and/or a portion of a support body to be coupled to the suture thread, a method of forming at least one hole, for example, holes 41 of FIG. 8C, in a support body, passing a suture thread through the hole, and tying suture threads together or tying a knot 42 of the suture thread to have a diameter greater than that of the hole of the support body, and a method of passing a suture thread passing through one hole to the opposite direction through another hole. However, the present invention is not limited thereto and a variety of methods may be employed (FIG. 1).

The suture thread having the support body of the present invention is used by being inserted in suturing needle or coupled to a needle accommodation body. A suture needle in use may be formed of a material such as metal that is not absorbed or an absorbable material such as polydioxanone (PDS). The suture needle may have a linear or curved shape overall. A needle tip may have a generally and widely used shape such as round or cut appearance.

A method of coupling the suture thread to the suture needle includes a method of inserting a suture thread in a hollow needle main body and pressing a needle, a method of forming a hole (needle eye) in a needle and inserting a suture thread in the hole, and a method of cutting a groove in a wall of a needle having a cavity and guiding a suture thread on the groove. However, the present invention is not limited thereto and other various methods may be employed therefor.

When suturing with a suture thread having the above-described support body, there is no need to separately tie a knot on a suture start portion and also the suture thread may be more firmly fixed than in a case of only tying a knot. This is useful not only for suturing an outer part of a human body but also for suturing an internal part of the human body such as an endoscope operation.

FIG. 2 illustrates the suture thread having the support body and a suturing needle according to an embodiment of the present invention. Referring to FIG. 2, a truncated circular cone type support body having a through-hole through both ends thereof is used. When a bottom surface of a support body having a larger diameter, like the support body, is arranged to face the suture needle, a firm knot effect may be obtained.

FIG. 3 illustrates a needle accommodation body according to an embodiment of the present invention and a suture thread having the needle accommodation body. Referring to FIG. 3, the needle accommodation body 20 is coupled to the suture thread 10 of the present invention. The needle accommodation body 20 has a shape of a tube with a through-hole through both ends thereof and also has a shape of a truncated circular cone or truncated pyramid in which a diameter of a through-hole increases from one end to the other end. The diameter of the through-hole of the needle accommodation body 20 is adjusted such that a needle may pass through and be inserted in the through-hole considering the diameter of a suturing needle to be used.

A method of coupling the suture thread to the needle accommodation body includes a method of melting an end of a suture thread and/or part of a needle accommodation body to be coupled to the suture thread to adhere the suture thread and the needle accommodation body and a method of forming at least one hole in a needle accommodation body, inserting a suture thread in the hole, and tying the suture thread into a knot or tying suture threads together. However, the present invention is not limited thereto and other various methods may be used therefor.

The suture needle 30 is coupled to the needle accommodation body. The suture needle 30 used in the present invention includes a needle main body 31 and a needle tip 32 formed at one end of the needle main body. The needle main body is formed to have a diameter that gradually increases from the needle tip to the other end of the needle main body. The suture needle is inserted in the needle accommodation body to which the suture thread is coupled and suturing is performed. At the final step of suturing, the suture needle penetrates other tissue around a suturing site, or penetrates or pierces other tissue around the suturing site so as to advance the needle accommodation body into the tissue. Then, the suture needle may be removed by pulling the suture needle toward a bottom end portion 21 of the needle accommodation body. Accordingly, the needle accommodation body without the suture needle 30 is left in the tissue and the suture thread used for suturing is still coupled to the needle accommodation body, and thus, suturing may not come untied without tying a knot at the final step of suturing.

Since the needle accommodation body has a shape of a circular cone or pyramid in which the diameter of the through-hole increases from one end portion to the other end portion of the needle accommodation body, part of the needle main body inserted in the needle accommodation body also has a diameter that gradually increases toward the other end thereof. Thus, when the suture thread is pulled after the suture needle is inserted into a suturing site during the suturing process, the suture needle is not disassembled from the needle accommodation body. To this end, the through-hole of the needle accommodation body has a size enough to accommodate the suture needle. Also, the size of the through-hole at a front end portion 22 of the needle accommodation body is less than that of a portion of the needle main body having a maximum diameter.

FIG. 4 illustrates the shapes of the needle accommodation body and the suture needle according to another embodiment of the present invention. As the needle accommodation body and part of the or the whole needle main body of the suture needle is formed larger than a bottom end portion of the needle accommodation body, a step is formed and thus the suture needle is prevented from being disassembled from the needle accommodation body when during suturing the suture needle is pulled in a direction in which suturing is performed. The needle accommodation body has a shape of a tube with a through-hole through both ends thereof and also has a shape of a truncated circular cone or truncated pyramid in which a diameter of a through-hole increases from one end to the other end (FIG. 4A) or has a shape of a circular column or a prism in which a diameter of a through-hole is constant (FIG. 4B). The suture thread is coupled to the needle accommodation body in the above-described method.

The suture needle used in the present invention may generally have a straight or curved shape. The needle tip may have a generally and widely used shape such as round or cutted appearance. The length and thickness of the needle tip may be adjusted suitably for a purpose thereof.

The needle accommodation body of the present invention may be formed of a material that is absorbable by a living body, for example, polylactic acid, polydiaxonone, copolymer of lactic acid and glycolic acid, etc, but the present invention is not limited thereto.

The present invention includes the suture thread of FIG. 5 to which the needle accommodation body is coupled to both ends of the suture thread, the suture thread of FIGS. 1-3 and 6-8 to which the needle accommodation body is coupled to one end of the suture thread and/or the support body is coupled to the other end thereof, and the suture thread of FIG. 9 to which the support bodies are coupled to both ends of the suture thread.

The suture thread used in the present invention includes a variety of shapes that are well known in the technical field to which the present invention pertains. The suture thread of the present invention may consist of one or two threads and may include at least one loop portion (FIGS. 6 and 7). FIG. 7A illustrates that the suture needle is inserted in the needle accommodation body. FIG. 7B illustrates that the suture needle is removed from the needle accommodation body.

In the present invention, a monofilament suture thread or a twisted suture thread, or a monofilament suture thread or twisted suture thread having barbs or cogs formed on an outer surface of the suture thread, may be used as the suture thread. A barbed suture thread is disclosed in Korean Patent Publication Nos. 10-2008-39345 and 10-2005-0108494, Korean Utility Model Publication No. 20-320005, and U.S. Pat. No. 5,931,855, the contents of which are incorporated in the present specification by reference. A barb may be arranged on a fiber according to a necessary configuration and may be formed by an appropriate method including well-known items in the technical field to which the present invention pertains. The methods may use a knife or laser, injection molding by press molding, stamping, or cutting. A required number of acute-angled cuts are made in a suture thread. The size of a barb may be adjusted suitably for a purpose within a reasonable range of the technical field to which the present invention pertains. For example, the depth of a barb formed in a suture thread may be about 30-100 microns, which may be adjusted according to the diameter of a suture thread. The interval between barbs formed on the outer surface of a suture thread may be 100 microns to 1 mm or higher.

FIG. 8 illustrates a barbed suture thread according to an embodiment of the present invention. Referring to FIG. 8A, two or more suture threads, each suture thread having a plurality of barbs that are inclined in the same direction in the front half portion and the rear half portion thereof at an angle of less than 90° or greater than 90° and less than 180° with respect to the lengthwise axis of the suture thread, are combined together. Then, one end of each of the suture threads is coupled to the suture needle and the other end of each of the suture threads is coupled to the support body. As another embodiment, referring to FIG. 8B, one or more suture threads having the barbs formed on the suture thread to be inclined in the opposite directions in the front half and rear half portions, for example, the barbs in the front half portion being all inclined at an angle of less than 90° with respect to the lengthwise axis of the suture thread toward the front end of the suture thread and the barbs in the rear half portion being all inclined at an angle of less than 90° with respect to the lengthwise axis of the suture thread toward the rear end of the suture thread, are half folded after passing through an eye of the suture needle. Then, both ends of each of the suture threads are coupled to the support body, or one end of each of the folded suture threads is inserted in the suture needle and pressed thereon and the other end thereof is coupled to the support body. Referring to FIG. 8C, the inclination directions of the barbs of the suture thread are different from those of the barbs of the suture thread of FIG. 8B. In this case, the suture thread is half folded after passing through the holes of the support body and two ends of the suture thread are coupled to the suture needle. For example, two, three, or four suture threads with barbs may be used and the number of suture threads may be adjusted according to the thickness or purpose of use of the suture thread. The directions of the barbs of the suture thread are schematically illustrated on the right side of each of FIGS. 8A, 8B and 8C. In an example of the suture thread of the present invention manufactured as above, as illustrated in FIG. 8, the barbs are inclined toward the support body, thus forming an acute angle with the lengthwise direction of the suture thread. When the barbs have the above shape, during suturing, the suture thread may smoothly proceed forward and also the barbs prevents the suture thread from proceeding in the opposite direction to a direction of the suturing. When the suture needle is cut off after finishing the suturing, the suture thread is not released due to the barbs and thus no knotting is needed. As such, when two or more suture threads with barbs are used by being coupled to the support body and/or the needle accommodation body, no knotting is needed and a more firm knotting effect may be obtained. Furthermore, compared to a case of using a suture thread with barbs that is typically used, one thread may snap during suturing because the strength of the suture thread is reduced to about half or more. However, when two or more suture threads are used, the strength of the suture threads may be increased to double or more and thus the suture threads may be less snapped. Furthermore, since the number of barbs or the contact surface of each barb are increased to double or more, more firm suturing may be obtained and the suture thread may be prevented from proceeding backward.

In another embodiment of the present invention, the support body is coupled to one end of the suture thread and the suture needle is coupled to the other end thereof, and a support body or the cone having a shape of a truncated circular cone or truncated pyramid and having a through-hole through both ends of the support body is inserted in the suture thread at a position close to the suture needle, as illustrated in FIG. 9. A truncated circular cone exhibiting less friction is more suitable as the cone. The cone is arranged such that a portion having a smaller diameter (front end) may face the suture needle and two knots A and B, each having a diameter larger than that of the front end, are respectively formed in front and rear of the front end (FIGS. 9A and 9B). The two knots A and B are formed close to each other. The knot A prevents the cone from escaping after suturing and the suture needle is removed. The knot B prevents the cone from being pushed backward during suturing. Even when suturing is completed and the suturing needle is removed, the cone is left at the end of the suturing thread. Thus, there is no need to make a knot after suturing and also there is no worry about untying of the suture thread. Another truncated circular cone or pyramid may be further provided in front of the knot A with a surface having a smaller diameter (front end) facing the suturing needle. Accordingly, the knot A may easily pass through tissue during suturing and thus suturing may be easily performed (FIG. 9B). A front cone is removed together when the suturing needle is removed after suturing and thus the knot A and the back cone may prevent the suturing thread from being released like FIG. 9A. The cone may be formed of, for example, an absorbable material such as copolymer of L-Lactide and Glycolide or a non-absorbable material such as polypropylene. The length of the cone may be, for example, about 1-10 mm. However, the present invention is not limited thereto and the length may be adjusted according to a site for use and purpose. The diameter of the through-hole through both ends of the support body of the cone may be, for example, about 0.1-2 mm at the front end having a relatively smaller diameter and about 0.5-5 mm at the rear end having a relatively larger diameter. However, the present invention is not limited thereto and the diameter may be adjusted according to a thickness and purpose of a suture thread.

In the suture thread with the barbs, one end of which is coupled to the support body (for example, FIG. 8), or the suture thread, one end of which is coupled to the support body and having a knot and cone formed at a portion close to a portion connected to the suture needle (for example, FIG. 9), provided according to the present invention, the other end of the suture thread that is not coupled to the support body may be coupled to the needle accommodation body or may be coupled directly to the suture needle for use. When the needle accommodation body functioning as a knot in a suturing site where suturing is completed is not used, the suture thread may not escape due to the barbs or the cone even when the suture needle is removed after suturing.

The suture thread provided according to the present invention may be formed of a non-absorbable material such as polypropylene, gold, stainless steel, titanium, nylon, polyvinyliden fluoride, polyester, braided silk, etc. or an absorbable material such as polydiaxonene, but the present invention is not limited thereto.

According to an embodiment of the present invention, a method of manufacturing a suture thread having a support body and/or a needle accommodation body includes operations of coupling one end of the suture thread to the support body and coupling the other end of the suture thread to the suture needle or the needle accommodation body.

The coupling of the suture thread to the support body includes applying heat to one end of the suture thread and/or the support body to melt the same and combining the suture thread and the support body having any one end or both ends melted. The coupling of the suture thread to the support body may additionally include lowering a temperature of a portion where the suture thread and the support body are coupled to each other. Furthermore, the method may include passing the suture thread through a hole formed in the support body or through a through-hole and then tying a knot on the suture thread to have a diameter larger than that of the hole of the support body or the through-hole. Furthermore, the method may include passing the suture thread through the hole formed in the support body or through the through-hole and then passing the suture thread in the opposite direction through another hole formed in the support body. When two suture threads are used, the present invention may include passing the suture threads through the hole formed in the support body or through the through-hole and then tying the suture threads together or tying the suture threads into a knot.

The coupling of the suture thread to the suture needle may include putting a suture thread in a suture needle having a through-hole formed therein and pressing the suture needle, inserting a suture thread in a hole formed in a suture needle, or hanging a suture thread on a cut formed in a wall of a suture needle having a through-hole.

The coupling of the suture thread to the needle accommodation body may include bonding by melting an end of the suture thread and/or part of the needle accommodation body to be coupled to the suture thread, and inserting the suture thread in at least one hole formed in the needle accommodation body and tying the suture thread into a knot or tying the suture thread together to be larger than the diameter of the hole.

According to an embodiment of the present invention, a method of manufacturing a suture thread includes operations of combining two suture threads, each suture thread having a plurality of barbs that are inclined in the same direction in the front half portion and the rear half portion of the suture thread, and coupling one end of each suture thread to a support body and the other end to a suture needle. Also, in another embodiment of the present invention, a suture thread having barbs that are inclined in the opposite directions in the front and rear half portions of the suture thread is half folded and then one end of the suture thread is coupled to a support body and the other end is coupled to a suture needle.

In another embodiment of the present invention, a method of manufacturing a suture thread includes operations of coupling a support body to one end of the suture thread, tying the suture thread into a knot at a portion close to the other end of the suture thread, inserting a truncated circular cone or truncated pyramid that has a through-hole through both ends thereof in the suture thread at the front side of a knot formed on the suture thread to have a front end having a relatively smaller diameter face a suture needle, tying the suture thread into a knot in front of the cone, and coupling the other end of the suture thread to the suture needle. The method may further include inserting an additional cone between the suture needle and the knot in front of the cone to have the front end having a relatively smaller diameter face the suture needle.

A suture thread formed by the above method is within a scope of the present invention. A method of suturing using a suture thread having a needle accommodation body according to the present invention includes operations of sewing a suturing site using a suture needle provided in the needle accommodation body to which the suture thread is coupled, advancing the suture needle through tissue around an end portion of the suturing site so that the needle accommodation body is buried in or passes through the tissue, and removing the suture needle by pulling the suture needle toward a bottom end portion of the needle accommodation body. When the needle accommodation body with the suture thread is buried in the tissue and fixed therein, an end of the suture thread is also connected to the needle accommodation body. Thus, there is no worry about untying of the suture thread and there is no need to tie a knot.

INDUSTRIAL APPLICABILITY

The suture thread, the needle accommodation body, and the suture thread support body according to the present invention may be useful for suturing in various surgical operations such as suturing of damaged muscles, blood vessels, nerves, injuries, or surgical cuts, double eyelid surgery, wrinkles plastic surgery, etc.

The invention claimed is:

1. A suture thread device comprising:
a thread comprising a first end portion and a second end portion; and
a needle accommodation body coupled to the first end portion of the thread, wherein the needle accommodation body has a shape of a tube having a through-hole through both ends in which a diameter of the through-hole increases from one end portion to the other end portion, wherein one or more holes are provided in a sidewall of the needle accommodation body, wherein the first end portion of the thread is coupled to the one or more holes of the sidewall, wherein the needle accommodation body is configured to receive a suture needle such that the suture needle is inserted in the through-hole.

2. The suture thread device of claim 1, further comprising another needle accommodation body coupled to the second end portion of the thread.

3. The suture thread device of claim 1, further comprising a suture thread support body coupled to the second end portion of the thread, the suture thread support body comprising one or more holes in which the thread is inserted, the suture thread support body having a diameter greater than that of the thread such that the suture thread support body inhibits the second end portion of the thread from being pulled into skin or tissue.

4. The suture thread device of claim 3, wherein the needle accommodation body, the suture thread support body, or the thread is formed of a material that is absorbable by a living body.

5. The suture thread device of claim 3, wherein the suture thread device further comprises one or more additional threads to form a loop portion.

6. A suture thread device comprising:
- two or more threads knotted together to form a knotted common end portion;
- a suture thread support body coupled to the knotted common end portion, the suture thread support body comprising a hole in which the two or more threads are inserted, the knotted common end portion having a size larger than that of the hole, the suture thread support body configured to inhibit the common end of the two or more threads from being pulled into skin or tissue; and
- a suture needle coupled to the other end of each of the two or more threads.

7. A needle accommodation body having a tube having a through-hole through both ends in which a diameter of the through-hole increases from one end portion to the other end portion, wherein one or more holes are provided in a sidewall of the needle accommodation body such that one end of a thread is coupled to the one or more holes of the sidewall, and the needle accommodation body is configured to receive a suture needle such that the suture needle is inserted in the through-hole.

* * * * *

UNITED STATES PATENT AND TRADEMARK OFFICE
CERTIFICATE OF CORRECTION

| | |
|---|---|
| PATENT NO. | : 9,848,865 B2 |
| APPLICATION NO. | : 14/840520 |
| DATED | : December 26, 2017 |
| INVENTOR(S) | : Young Jae Kim |

It is certified that error appears in the above-identified patent and that said Letters Patent is hereby corrected as shown below:

On the Title Page

Item (56), on page 3, right column, at Line 37, change "*uropean*" to --*European*--.

Item (56), on page 3, right column, at Line 39, change "*merriram*" to --*merriam*--.

In the Specification

In Column 3, at Line 56, change "*invention;*" to --*invention.*--.

In Column 4, at Lines 50-51, change "poly*(vinyldene fluoride)*" to --*poly(vinylidene fluoride)*--.

In Column 4, at Line 55, change "*polydiaxonone,*" to --*polydioxanone,*--.

In Column 6, at Line 53, change "*polydiaxonone,*" to --*polydioxanone,*--.

In Column 9, at Line 13, change "*polydiaxonene,*" to --*polydioxanone,*--.

Signed and Sealed this
Fifth Day of March, 2019

Andrei Iancu
*Director of the United States Patent and Trademark Office*